United States Patent [19]

Kaplan et al.

[11] 4,192,817

[45] * Mar. 11, 1980

[54] AMPHOTERIC SURFACTANTS

[75] Inventors: Saul Kaplan, Teaneck; John J. Merianos, Jersey City, both of N.J.; Harold A. Green, Havertown, Pa.; Alfonso N. Petrocci, Glen Rock, N.J.

[73] Assignee: Kewanee Industries, Inc., Bryn Mawr, Pa.

[ * ] Notice: The portion of the term of this patent subsequent to Jan. 9, 1996, has been disclaimed.

[21] Appl. No.: 943,376

[22] Filed: Sep. 18, 1978

Related U.S. Application Data

[60] Continuation-in-part of Ser. No. 848,071, Nov. 23, 1977, Pat. No. 4,133,772, which is a division of Ser. No. 799,697, May 23, 1977, Pat. No. 4,076,744.

[51] Int. Cl.$^2$ ........................ C07C 143/02; A01N 9/20

[52] U.S. Cl. ................................ 260/513 N; 424/325

[58] Field of Search .................................... 260/513 N

[56] References Cited

U.S. PATENT DOCUMENTS

| | | | |
|---|---|---|---|
| 4,076,744 | 2/1978 | Kaplan | 260/501.19 |
| 4,133,772 | 1/1979 | Kaplan | 252/106 |

*Primary Examiner*—Alan Siegel

*Attorney, Agent, or Firm*—Arthur A. Jacobs

[57] ABSTRACT

The products of the reaction between one mol of $$RNHCH_2CH_2NHCH_2CH_2NH\overset{O}{\overset{\|}{C}}CH_2\underset{SO_3M'''}{\underset{|}{CH}}-\overset{O}{\overset{\|}{C}}-OM^{iv}$$

and one mol of $$ClCH_2\overset{O}{\overset{\|}{C}}-ONa$$

are self-preserving, non-irritating, amphoteric surfactants; R representing an alkyl group of from 8 to 14 carbon atoms and M''' and $M^{iv}$ representing the same or different moieties selected from the group consisting of hydrogen, alkali metals, ammonium and ammonium substituted by from 1 to 3 lower alkyl groups, such alkyl groups each being optionally substituted by one hydroxyl group.

4 Claims, No Drawings

AMPHOTERIC SURFACTANTS

The application is a continuation-in-part of application Ser. No. 848,071 filed Nov. 23, 1977 now U.S. Pat. No. 4,133,772, which, in turn, is a division of application Ser. No. 799,697, filed May 23, 1977 and now issued as U.S. Pat. No. 4,076,744 dated Feb. 28, 1978, both of which are incorporated by reference herein.

The aforesaid applications disclosed a method of preparing compounds of the type

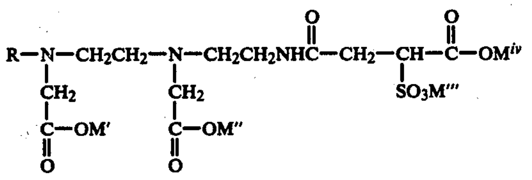

in which R represents an alkyl group of from 8 to 14 carbon atoms, and M', M''', M and $M^{iv}$ represent the same or different moieties selected from the group consisting of hydrogen, alkali metal, ammonium, and ammonium substituted by from 1 to 3 lower alkyl groups, such alkyl groups each being optionally substituted by one hydroxyl group; this method of synthesis has its origin in causing one mole of

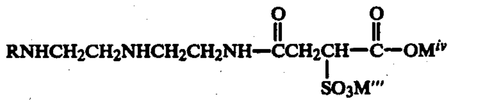

to react with 2 moles of

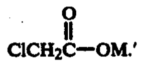

The properties of the products of the aforesaid synthesis were disclosed as being those of self-preserving, non-irritating, anionic-surfactant-compatible, amphoteric surfactants.

It was furthermore disclosed in the aforesaid applications that compounds of the type described in the disclosures, but having only one carboxymethyl group

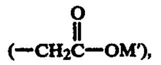

instead of two carboxymethyl groups, have about the same self-preserving non-irritating, anionic-surfactant-compatability properties as their related compounds.

The aforesaid application also disclosed the method of synthesizing compounds having only one carboxymethyl group by causing one mol of

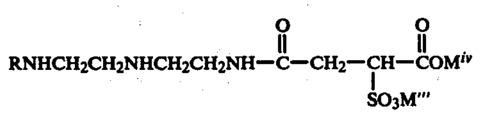

to react with only one mol of

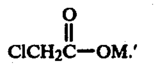

Products of the latter type of synthesis comprise the present invention.

EXAMPLE 1

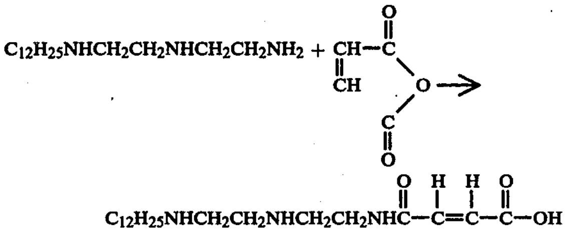

155 grams of N-dodecyl diethylenetriamine (0.57 moles) are dissolved in 57 grams of isopropanol with the aid of a little heat, and 57 grams of maleic anhydride (0.58 moles) are dissolved in 57 grams of isopropanol with the aid of a little heat.

With both solutions at a temperature slightly below 50° C., the maleic anhydride solution is added to the amine solution in small increments, over a period of about ½ hour, with constant stirring. An ice bath is used to keep the temperature of the reaction mixture below about 50° C., but the reaction temperature is kept above about 40° C. to speed up the reaction.

After addition is complete, the reaction mixture is kept at about 35°-40° C. with constant stirring for about 1½ hours.

The mixture weighs 328 grams. Upon analysis, it was found to contain about 1.79 milli-equivalents of free carboxylic acid groups per gram. The calculated concentrations for free carboxylic acid groups is 1.74 milli-equivalents per gram. The slight excess of carboxylic acid groups over theory was due to the 0.01 mole excess of maleic anhydride reactant which accounts for 2 milli-equivalents of free carboxylic acid group per milli-mole of anhydride.

The analysis can be interpreted to means that the yield is about 100%.

EXAMPLE 2

The reaction of Example 1 is repeated, except that N-decyl diethylenetriamine and N-tetradecyl diethylenetriamine respectively replace N-dodecyl diethylenetriamine as a reactant, all reactants being used in about the same molar ratios. The results duplicate those found in Example 1.

EXAMPLE 3

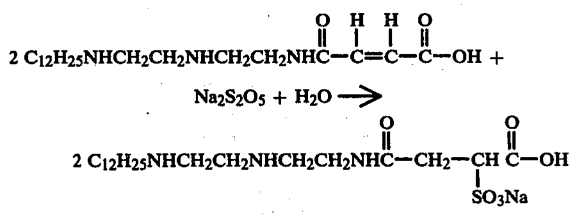

200 grams of the final mixture product of Example 1, without further purification, are dissolved in about 100 grams of water and warmed to about 40° C., at which temperature 33 grams of solid $Na_2S_2O_5$ is added in one increment. This raises the temperature only slightly so the mixture is heated, with stirring, to 66° C., and kept at about that temperature for 2 hours. The final mixture weighs 328 grams.

Calculations indicated that it contains about 2.15 milli-equivalents of free available amine per gram.

EXAMPLE 4

The reaction of Example 3 is repeated, except that each of the two products in Example 2 replaces the product of Example 1, all reactants being used in about the same molar ratios. The results are similar to those of Example 3.

EXAMPLE 5

To 96 grams of the product mixture from Example 3 (containing about 208 milli-equivalents of free available amino nitrogen) is added about 12.9 grams of 97% pure sodium chloroacetate (about 107 milli-moles) which represents 1 milli-equivalent of sodium chloroacetate plus about 3% excess for every 2 milli-moles of free available amino nitrogen.

The mixture is warmed gently and the pH taken about every 10 minutes using a calomel electrode. As the reaction proceeds, the pH falls, but it is restored continuously by the dropwise addition of about 30% aqueous sodium hydroxide. In this manner, the reaction is run at a temperature of about 85° C., while the pH is maintained between 6.7 and 8.0.

Ionic chloride determinations are made periodically to estimate the extent of the reaction, and the reaction is considered to be complete when analysis for ionic chlorine is equal to the calculated amount, which in this case is about 107 milli-equivalents in the entire mixture.

The reaction is completed in about 2-4 hours. As the reaction nears completion, the pH of the reaction mixture remains almost constant.

EXAMPLE 6

The reaction of Example 5 is repeated, except that each of the two products made in Example 4 is substituted for the product made in Example 3, all reactants being used in about the same molar ratios. The results are similar to those described in Example 5.

EXAMPLE 7

Eye irritation was determined by the procedure suggested by Dr. Draize as described in "Appraisal of the Safety of Chemicals in Foods, Drugs, and Cosmetics" published by the Association of Food and Drug Officials of the United States.

Each of three normal healthy albino rabbits had 0.1 ml. of 7½% solids, in aqueous solution, of the compound of Example 5, instilled into the right eye, with no further subsequent treatment. The left eye of each animal was left untreated and was used as a control.

Both eyes were examined every 24-hours for 4 days, and again on the seventh day; these observations were recorded on the Draize scale for scoring occular lesions. All recordings were zero for all observations on each animal with regard to changes in cornea, changes in iris, and conjunctivitis.

EXAMPLE 8

The compositions were tested for preservative ability in the following manner:

50 gram samples from each composition were transferred to sterile 4-ounce, wide-mouth jars. Two replicate jars were prepared for every sample, including an untreated control.

Each jar was inoculated with 2.5 ml. of a 1/10 sterile nutrient heated dilution of pooled 24-hour broth cultures of Staphylococcus aureus, Pseudomonas aeruginosa, Escherichia coli, Enterobacter aerogenes, Proteus species and Bacillus species. In this manner, a bacterial challenge load of $(1-10)\times 10^6$ organisms/ml. of jar content was obtained.

All inoculated jars were stored at 25° C.-27° C. At weekly intervals following inoculation, a one ml., aliquot of jar content was removed from each jar, and a tenfold serial dilution was prepared therefrom in sterile "Azlectin"/"Tween 80" neutralizer solution which was then placed into a TGE jar.

In this manner, the number of surviving organisms was determined.

All jars were stored for 8 consecutive weeks, and weekly platings were prepared therefrom for the purpose of counting the surviving viable bacteria. Adequate preservation was considered to be achieved when 99.9% of the organism load used to inoculate the sample were killed.

In those instances where no viable surviving organisms were observed at four weeks following inoculation or before, the jar contents were re-inoculated after the fourth week exactly as previously described in the inoculation procedure.

Four additional weekly platings and countings were made for each jar, making a total of 8 consecutive weekly observations following the initial inoculation.

Following is a table showing the results of the tests for preservation. The bacterical count after each week is listed for each of the products tested. The asterisk indicates that the number must be multiplied by $10^6$.

In this table, the following designations represent the products under test and the conditions under which they were tested.

The following notations are used to identify the materials that were tested for preservation.

"A"—the compound in which R is $C_{10}H_{21}$—, at a concentration of 7.5%.

"B"—the compound in which R is $C_{10}H_{21}$—, at a concentration of 12.5%, together with sodium lauryl sulfate at a concentration of 2.5%.

"C"—the compound in which R is $C_{12}H_{25}$—, at a concentration of 7.5%.

"D"—the compound in which R is $C_{12}H_{25}$—, at a concentration of 12.5%, together with sodium lauryl sulfate at a concentration of 2.5%.

Example 9

| | Bacterial Count At Weekly Intervals | | | |
|---|---|---|---|---|
| End of week | A | B | C | D |
| 1 | 210 | 210 | 90,000 | 98,000 |
| 2 | 210 | 210 | 210 | 210 |
| 3 | 210 | 210 | 210 | 210 |
| 4 | 210 | 210 | 210 | 210 |
| Reinoculation | | | | |
| 5 | 210 | 210 | 44,000 | .16* |
| 6 | 210 | 210 | 210 | 210 |
| 7 | 210 | 210 | 210 | 210 |
| 8 | 210 | 210 | 210 | 210 |

*Indicates that the number must be multiplied by $1\times 10^6$

The invention claimed is:

1. An antimicrobial compound made by reacting a compound of formula $$RNH-CH_2CH_2NHCH_2CH_2NH\overset{\overset{\displaystyle O}{\|}}{C}-CH_2-\underset{\underset{\displaystyle SO_3M'''}{|}}{CH}-\overset{\overset{\displaystyle O}{\|}}{C}-OM^{iv}$$

with an approximately equimolar quantity of sodium chloroacetate while adding sodium hydroxide at a rate which keeps the pH of the reaction mixture approximately between 6.5 and 8.5 until the reaction is substantially complete, R being a normal alkyl group of from 8 to 18 carbon atoms and M''' and $M^{IV}$ being the same or different and selected from the group consisting of hydrogen, alkalai metals, ammonium and ammonium substituted by from 1 to 3 lower alkyl groups, said lower alkyl groups being optionally substituted by one hydroxyl group.

2. The compound made according to claim 1 in which R is the n-dodecyl group.

3. The compound made according to claim 1 in which R is the n-decyl group.

4. The compound made according to claim 1 in which R is the n-tetradecyl group.

* * * * *